United States Patent
Bernstein et al.

(10) Patent No.: US 6,909,815 B2
(45) Date of Patent: Jun. 21, 2005

(54) METHOD FOR PERFORMING AUTOMATED IN-SCENE BASED ATMOSPHERIC COMPENSATION FOR MULTI-AND HYPERSPECTRAL IMAGING SENSORS IN THE SOLAR REFLECTIVE SPECTRAL REGION

(75) Inventors: Lawrence S. Bernstein, Lexington, MA (US); Steven M. Adler-Golden, Newtonville, MA (US); Timothy C. Perkins, Brighton, MA (US); Alexander Berk, Canton, MA (US); Robert Y. Levine, Bedford, MA (US)

(73) Assignee: Spectral Sciences, Inc., Burlington, MA (US)

( * ) Notice: Subject to any disclaimer, the term of this patent is extended or adjusted under 35 U.S.C. 154(b) by 138 days.

(21) Appl. No.: 10/356,060

(22) Filed: Jan. 31, 2003

(65) Prior Publication Data

US 2004/0153284 A1 Aug. 5, 2004

(51) Int. Cl.$^7$ ............................................ G06K 9/40
(52) U.S. Cl. ........................................... 382/274
(58) Field of Search ............................. 382/274; 702/2, 702/4; 703/4

(56) References Cited

U.S. PATENT DOCUMENTS

| | | | | |
|---|---|---|---|---|
| 5,315,513 A | * | 5/1994 | Abreu et al. ................. | 702/3 |
| 6,677,885 B1 | * | 1/2004 | Frankot ..................... | 342/25 R |
| 6,834,125 B2 | * | 12/2004 | Woodell et al. ............. | 382/274 |

OTHER PUBLICATIONS

Anderson, "FLAASH and MODTRAN4: State-of-the-Art Atmospheric Correction for Hyperspectral data", Aerospace Conference, 1999. Proceedings. 1999 IEEE, vol.: 4, Mar. 6–13, 1999 pp.: 177–181 vol. 4.*

A. Berk, L.S. Bernstein, G.P. Anderson, P.K. Acharya, D.C. Robertson, J.H. Chetwynd and S.M. Adler–Golden, "MODTRAN Cloud and Multiple Scattering Upgrades with Application to AVIRIS," Remote Sensing Environment 65, 367, 1998.

(Continued)

Primary Examiner—Jose L. Cougo
Assistant Examiner—Tom Y. Lu
(74) Attorney, Agent, or Firm—Brian M. Dingman, Esq.; Mirick, O'Connell, DeMaillie & Lougee, LLP

(57) ABSTRACT

A method of automatically compensating a multi- or hyper-spectral, multi-pixel image for atmospheric effects, comprising resolving a plurality of spectrally-diverse pixels from the image, determining a spectral baseline from the spectrally-diverse pixels, determining a statistical spectral deviation of the spectrally-diverse pixels, normalizing the statistical spectral deviation by applying a scale factor, and compensating image pixels with both the spectral baseline and the normalized spectral deviation. Another embodiment features a method of automatically determining a measure of atmospheric aerosol optical properties using a multi- or hyper-spectral, multi-pixel image, comprising resolving a plurality of spectrally-diverse pixels from the image, determining a statistical spectral deviation of the spectrally-diverse pixels, correcting the statistical spectral deviation for non-aerosol transmittance losses, and deriving from the statistical spectral deviation one or more wavelength-dependent aerosol optical depths. A final embodiment features a method of automatically determining a measure of atmospheric gaseous optical properties using a multi- or hyper-spectral, multi-pixel image, comprising resolving a plurality of spectrally-diverse pixels from the image, determining a statistical spectral deviation of the spectrally-diverse pixels, and deriving from the statistical spectral deviation wavelength-dependent gaseous optical depths.

26 Claims, 9 Drawing Sheets

OTHER PUBLICATIONS

P.S. Chavez, "An Improved Dark–Object Subtraction Technique for Atmospheric Scattering Correction of Multispectral Data," Remote Sensing of Environment, vol. 24, pp. 459–479, 1988.

R. Richter, "Atmospheric Correction of DAIS Hyperspectral Image Data," SPIE AEROSENSE '96 Conference, Orlando, FL, Apr. 8–12, SPIE Proceedings, 2758, 1996.

Y.J. Kaufman, D. Tanre, L.A. Remer, E.F. Vermote, A. Chu, and B.N. Holben, "Operational Remote Sensing of Tropospheric Aerosol over Land from EOS Moderate Imaging Spectroradiometer," J. Geophys Res. 102, 17051, 1997; Y.J. Kaufman, A.E. Wald, L.A. Remer, B.–C. Gao, R.–R. Li, and L. Flynn, "The MODIS 2.1–um Channel–Correlation with Visible Reflectance for Use in Remote Sensing of Aerosol," IEEE Transactions on Geoscience and Remote Sensing, 35, pp. 1286–1298, 1997.

B.–C. Gao, K.B. Heidebrecht and A.F.H. Goetz, Atmosphere Removal Program (ATREM) Version 2.0 Users Guide, Center for the Study of Earth from Space/CIRES, University of Colorado, Boulder, Colorado, 26 1996.

S.M. Adler–Golden, M.W. Matthew, L.S. Bernstein, R.Y. Levine, A. Berk, S.C. Richtsmeier, P.K. Acharya, G.P. Anderson, G. Felde, J. Gardner, M. Hoke, L.S. Jeong, B. Pukall, J. Mello, A. Ratkowski and H.–H. Burke, Atmospheric Correction for Short–wave Spectral Imagery based on MODTRAN4, SPIE Proceeding, Imaging Spectrometry V, 3753, pp. 61–69, 1999.

* cited by examiner

METHOD FOR PERFORMING AUTOMATED IN-SCENE BASED ATMOSPHERIC COMPENSATION FOR MULTI-AND HYPERSPECTRAL IMAGING SENSORS IN THE SOLAR REFLECTIVE SPECTRAL REGION

GOVERNMENT RIGHTS

This invention was made with Government support under Contract F19628-02-C-0054 awarded by the Department of the Air Force. The Government has certain rights in this invention.

FIELD OF INVENTION

This invention relates to automated methods for correcting multi- and hyperspectral images of the earth's surfaces for atmospheric effects and sensor calibration problems.

BACKGROUND OF THE INVENTION

The problem addressed here is the compensation of remotely sensed multi- and hyperspectral images in the solar reflective spectral regime ($\lambda$<3000 nm) for the transmission losses and scattering effects of the intervening atmosphere. The problem is illustrated in FIG. 1 for a pixel containing vegetation as viewed from a space-based sensor. A number of large spectral depressions are seen which are primarily due to absorption by gaseous water and to a lesser extent by carbon dioxide and oxygen. Below 700 nm, the observed reflectance exceeds the actual reflectance; this is due to atmospheric scattering by aerosols and molecules. The apparent reflectance at the sensor is well represented by $$\rho_j(\lambda) = A(\lambda) + B(\lambda)\rho_j^o(\lambda) + C(\lambda)<\rho(\lambda)>, \quad (1)$$

where $\rho_j$ is the observed reflectance (the radiance normalized by the surface normal component of the solar flux) for the j'th pixel at a spectral band centered at wavelength $\lambda$, $\rho_j^o$ is the actual surface reflectance, $<\rho>$ is a spatially averaged surface reflectance, and A, B, and C are coefficients representing the transmission and scattering effects of the atmosphere. The first coefficient, A, accounts for light which never encounters the surface and is scattered and absorbed within the atmosphere. The second, B, accounts for the sun-surface-sensor path transmittance loss. The third, C, accounts for the adjacency effect which is the cross talk between pixels induced by atmospheric scattering. The length scale of the adjacency effect is typically of order ~0.5 km, thus $<\rho>$ is a slowly varying function of position within a large image. It is noted that B and C also have a weak dependence on $<\rho>$ through light that reflects off the surface and is scattered back to the surface by the atmosphere.

The aim of atmospheric compensation is to determine A, B, C and $<\rho>$ by some means in order to invert Eq(1) to retrieve the actual surface reflectance, $\rho_j^o$. The prior art is embodied in various methods described in the literature and summarized below.

The simplest and computationally fastest prior art methods for atmospheric correction are the "Empirical Line Method" (ELM) and variants thereof, which may be found in the ENVI (Environment for Visualizing Images) software package of Research Systems, Inc. The ELM assumes that the radiance image contains some pixels of known reflectance, and also that the radiance and reflectance values for each wavelength channel of the sensor are linearly related, in the approximation that A, B, C and $<\rho>$ are constants of the image. Therefore, the image can be converted to reflectance by applying a simple gain and offset derived from the known pixels. This method is however not generally applicable, as in-scene known reflectances are often not available. In variants of the ELM, approximate gain and offset values are generated using pixels in the image that are treated as if their spectra were known. For example, in the Flat Field Method a single bright pixel is taken as having a spectrally flat reflectance and the offset is taken as zero; accordingly, dividing the image pixel spectra by the bright pixel spectrum yields approximate relative reflectances. In the Internal Average Relative Reflectance method this procedure is followed using a scene-average spectrum rather than a single bright pixel spectrum. In general, neither the Flat Field Method nor the Average Relative Reflectance methods are very accurate.

More sophisticated prior art methods are based on first-principles computer modeling. These methods require extensive, and often time-consuming, calculations with a radiative transfer code, such as MODTRAN [Berk et al., 1998], in which A, B and C are computed for a wide range of atmospheric conditions (aerosol and water column amounts and different surface reflectance values). The calculations may be performed for each image to be analyzed, or may be performed ahead of time and stored in large look-up tables. The appropriate parameter values for the image are determined by fitting certain observed spectral features, such as water vapor absorption bands, to the calculations. For retrieving aerosol or haze properties such as the optical depth, methods are available that rely on "dark" pixels, consisting of vegetation or dark soil [Kaufman et al., 1997] or water bodies. Commonly used first-principles computer codes for atmospheric correction include: ATREM [Gao et al., 1996]; ACORN [R. Green, unpublished], available from Analytical Imaging and Geophysics LLC; FLAASH [Adler-Golden et al., 1999], developed by Spectral Sciences Inc. (SSI) and the Air Force Research Laboratory (AFRL); and ATCOR2 [Richter, 1996], used mainly for multispectral atmospheric correction.

SUMMARY OF THE INVENTION

The invention includes both a complete atmospheric correction method, and methods for retrieving the wavelength-dependent optical depth of the aerosol or haze and molecular absorbers. The atmospheric correction method of the current invention, unlike first-principles methods, allows the retrieval of reasonably accurate reflectance spectra even when the sensor does not have a proper radiometric or wavelength calibration, or when the solar illumination intensity is unknown, such as when a cloud deck is present. The computational speed of the atmospheric correction method is superior to that of first-principles methods, making it potentially suitable for real-time applications. The invention determines the atmospheric compensation parameters directly from the information contained within the scene (observed pixel spectra).

The aerosol optical depth retrieval method of the current invention, unlike prior art methods, does not require the presence of dark pixels. The retrieved optical depth information can be utilized to improve the accuracy of methods that use first-principles modeling. In particular, it can be used to set the optical depth of a model aerosol when dark pixels are unavailable, or to select from among alternative model aerosols to provide consistency between optical depths retrieved from a dark pixel method and from the current invention.

The underlying assumptions of the invention are:

1. There are a number (≈10 or more) of diverse pixel spectra (diverse materials) in the scene, and 2. The spectral standard deviation of $\rho_j^o$ for a collection of diverse materials is a nearly wavelength-independent constant.

An additional, helpful assumption is:

3. There are sufficiently dark pixels ($\rho_{jo}(\lambda) \approx 0$) in a scene to allow for a good estimation of the nearly spatially invariant baseline contribution, $\rho_b = A + C <\rho>$.

The first assumption is virtually always applicable, as it only requires that a handful of pixels out of typically ~$10^5$ to $10^6$ pixels display diverse spectra. The most notable exception would be a scene over completely open and deep water, in which case the material reflectance is well known a priori. The diverse spectra can be selected using any of a number of spectral diversity metrics and algorithms. The second assumption appears to be generally true based on empirical observation and is likely related to the lack of spectral correlation between diverse materials. The third assumption is frequently applicable, as most scenes will contain a number of very dark pixels from such surfaces as water bodies, vegetation, and cast shadows. For the atypical cases that violate this assumption, there are methods, described below, for estimating a reasonable baseline.

Under these assumptions, the spectral standard deviation of Eq(1) for a set of diverse pixel spectral can be expressed as, $$\sigma\rho(\lambda) = B(\lambda)\sigma\rho^o(\lambda). \tag{2}$$

There is no contribution to the standard deviation from A or $C<\rho>$ because they are the same for each pixel spectrum. Since $\sigma\rho^o$ is assumed to be constant, then to within a normalization factor, designated $g_o$, $\sigma\rho$ represents one of the correction factors, B. The actual surface spectral reflectance can be retrieved using the extracted in-scene determined compensation parameters via $$\rho_j^o(\lambda) = \frac{\rho_j(\lambda) - \rho_b(\lambda)}{g_o \sigma\rho(\lambda)}. \tag{3}$$

A key attribute of this invention is its applicability to any sensor viewing or solar elevation angle.

There are a number of methods to establish the normalization factor $g_o$, which depends on sensor attributes. For many sensors there is at least one atmospheric window band, typically in the 1500–2500 nm region (see FIG. 1), for which $B(\lambda) \approx 1$ (inspection of FIG. 1 shows that B=0.9 is a good estimate); thus for this band $$g_o = 0.9/\sigma\rho. \tag{4}$$

If a suitable window band is not available, the normalization can still be extracted directly from the standard deviation curve. Two bands ($\lambda_2 > \lambda_1$) are selected which are outside of any water absorption region, insuring that the atmospheric extinction is due primarily to the aerosols. The ratio of the standard deviations of these bands is a direct measure of the difference in aerosol optical depth $\tau$ via, $$-\ln\frac{\sigma\rho(\lambda_1)}{\sigma\rho(\lambda_2)} = \tau(\lambda_1) - \tau(\lambda_2). \tag{5}$$

Depending on the wavelengths of the selected bands, a generally small correction for molecular Rayleigh scattering may be required. Standard and efficient methods are available for applying this correction.

For aerosols, the ratio of optical depths at two wavelengths is well approximated by the Angstrom formula, $$\frac{\tau(\lambda_1)}{\tau(\lambda_2)} = \left(\frac{\lambda_2}{\lambda_1}\right)^\alpha, (\alpha > 0). \tag{6}$$

For terrestrial aerosols $\alpha$ falls in the range $1 > \alpha > 2$, and we adopt $\alpha = 1.5$ for general estimation purposes. Combining Eqs. (5) and (6) allows one to convert the optical depth difference to an absolute optical depth at either wavelength, $$\tau(\lambda_2) = \frac{-\ln\frac{\sigma\rho(\lambda_1)}{\sigma\rho(\lambda_2)}}{\left(\frac{\lambda_2}{\lambda_1}\right)^\alpha - 1}. \tag{7}$$

The normalization factor is now determined from $$g_o = \exp(-\tau(\lambda_2))/\sigma\rho(\lambda_2). \tag{8}$$

It is noted that Eq(8) is just the generalization of Eq(4).

If the sensor radiometric calibration or the solar illumination intensity are not known, then $\sigma\rho$ is known only to within a scale factor, and the normalization factor go must be estimated by a different method. One method is to set $g_o$ such that that the maximum retrieved reflectance value for any wavelength and pixel is unity. This method is found to work reasonably in images containing a diversity of man-made materials, such as urban scenes. Another method is to derive $g_o$ by comparing the retrieved reflectance values with those in a library of material spectra.

For most scenes, the baseline curve is defined as the darkest observed signal for each band from among the diverse spectra. The presence of sufficiently dark pixels is indicated by at least one pixel spectrum with an apparent reflectance below ~0.05 for $\lambda > 1500$ nm. For the rare situation that a dark spectrum is unavailable, it is still possible to estimate a reasonable background. It is worth noting that this case arises because the pixel reflectances are generally much larger than the baseline contribution, thus considerable uncertainty in the baseline values are tolerable. In this case, the baseline may be approximated as the excess reflectance at the shorter wavelengths (where baseline effects are most important) relative to a flat spectral reflectance material, $$\rho_b(\lambda) = \rho_b^o(\lambda) - \beta\sigma\rho(\lambda), (\lambda < 1000 \text{ nm}), \tag{9}$$

where $\rho_b^o$ is an initial baseline guess defined by the darkest available channels, and $\beta$ is adjusted such that $\rho_b = 0$ at 1000 nm (or some suitably nearby channel depending on the available sensor bands). The baseline is taken as zero for $\lambda > 1000$ nm. An alternative method is to use a radiative-transfer code to compute the baseline based on the retrieved aerosol and molecular optical properties. Other methods for estimating the baseline spectrum will be known to those skilled in the art. These include a pairwise linear regression method [Crippen, 1987] and a dark pixel method that incorporates a theoretical representation of the baseline's wavelength dependence [Chavez, 1988].

While the focus of the previous discussion was on atmospheric compensation, it was noted that this invention provides, to within a normalization factor, the sun-surface-sensor path transmittance $B(\lambda)$. Analysis of B can provide quantitative measures (column amounts) of all the atmospheric attenuation sources, including aerosol scattering and absorption and molecular absorption and Rayleigh scattering. This may be accomplished through spectral fitting with an accurate atmospheric radiative-transfer code (e.g., MODTRAN), or alternatively through the use of analytical approximations. Of most significance is that one can extract the detailed wavelength dependence of the aerosol extinction which has not been accessible with previous multi- and hyperspectral image analysis approaches.

It should be noted that the definition of a scene or image is flexible, in that it may include a sub-section of pixels from a larger original data set. Thus, the current invention may be applied to individual sub-sections of a scene or image, provided that a sufficient diversity of pixel spectra exists within the sub-sections for computing an accurate standard deviation and baseline. In this way, spatial variations in the adjacency averaged reflectance <ρ> and in the atmospheric parameters can be identified and taken into account in the atmospheric correction.

This invention features in one embodiment a method of automatically compensating a multi- or hyper-spectral, multi-pixel image for atmospheric effects, comprising resolving a plurality of spectrally-diverse pixels from the image, determining a spectral baseline from the spectrally-diverse pixels, determining a statistical spectral deviation of the spectrally-diverse pixels, normalizing the statistical spectral deviation by applying a scale factor, and compensating image pixels with both the spectral baseline and the normalized spectral deviation.

The compensating step may comprise subtracting the spectral baseline from the image pixels to accomplish partially-compensated pixels, and further, dividing the partially-compensated pixels by the normalized spectral deviation. The resolving step may take place with a spectral end member selection algorithm or a clustering algorithm, and may be accomplished manually. At least ten end members may be resolved. The resolving step may take place using a subset of spectral bands that span the spectrum of the image.

The method may further comprise screening anomalous pixels out of the image pixels before the resolving step. The screening step may comprise removing pixels containing opaque clouds and cirrus clouds.

The spectral baseline determining step may take place using a linear regression method. The spectral baseline determining step may comprise determining the excess reflectance at relatively short wavelengths relative to a flat spectral reflectance material, or may comprise determining the darkest signal from all of the image pixels for each spectral band, or determining the darkest signal in any spectral band from all of the spectrally-diverse pixels, or subtracting a constant reflectance contribution. The spectral baseline determining step in this case may further comprise setting the constant reflectance contribution to match the image signal at a reference wavelength. The spectral baseline determining step may use a radiative-transfer code to compute the baseline based on the determined aerosol and molecular optical properties The statistical spectral deviation determining step may comprise determining the standard deviation of the spectrally-diverse pixels. The normalizing step may comprise normalizing in a spectral band in which the sun-surface-sensor path spectral transmittance factor is close to unity, or resolving at least two spectral window bands that do not have a significant contribution from water absorption, using the spectral deviations of these window bands to retrieve an aerosol optical depth, and using the optical depth to normalize. The normalizing step may involve establishing the scale factor such that the maximum retrieved reflectance value for any wavelength and pixel of the spectrally-diverse pixels is unity. Alternatively, the normalizing step may comprise comparing the spectrally-diverse pixels to a predetermined set of spectra of different, known materials.

The image compensation method may further comprise refining the spectrally-diverse pixels to remove spectrally-diverse pixels that contain undesirable spectral features, the refining step taking place after the normalizing step and before the compensating step. This refining step may comprise removing pixels with an abrupt reflectance change around about 700 nm, or removing pixels that have the greatest effect on the smoothness of the statistical spectral deviation, or introducing a wavelength dependence into a normalization factor such that selected spectrally-diverse pixels are made to agree with corresponding known library spectra as closely as possible.

This invention features in another embodiment a method of automatically determining a measure of atmospheric aerosol optical properties using a multi- or hyper-spectral, multi-pixel image, comprising resolving a plurality of spectrally-diverse pixels from the image, determining a statistical spectral deviation of the spectrally-diverse pixels, correcting the statistical spectral deviation for non-aerosol transmittance losses, and deriving from the statistical spectral deviation one or more wavelength-dependent aerosol optical depths.

The statistical spectral deviation determining step may comprise determining the standard deviation of the spectrally-diverse pixels. The correcting step may involve using a radiative transfer code. The deriving step may also involve using a radiative transfer code. The deriving step may alternatively comprises performing a least squares fit of the statistical spectral deviation to an analytical representation of the aerosol transmittance, or performing a least squares fit of the statistical spectral deviation to a radiative transfer code.

In a final embodiment, this invention features a method of automatically determining a measure of atmospheric gaseous optical properties using a multi- or hyper-spectral, multi-pixel image, comprising resolving a plurality of spectrally-diverse pixels from the image, determining a statistical spectral deviation of the spectrally-diverse pixels, and deriving from the statistical spectral deviation wavelength-dependent gaseous optical depths.

The statistical spectral deviation determining step may comprise determining the standard deviation of the spectrally-diverse pixels. The deriving step may comprise selecting spectral bands that are outside of any water absorption region, and deriving a gaseous optical depth from the statistical spectral deviations at the selected bands.

DETAILED DESCRIPTION OF THE PREFERRED EMBODIMENTS

Figure 1:
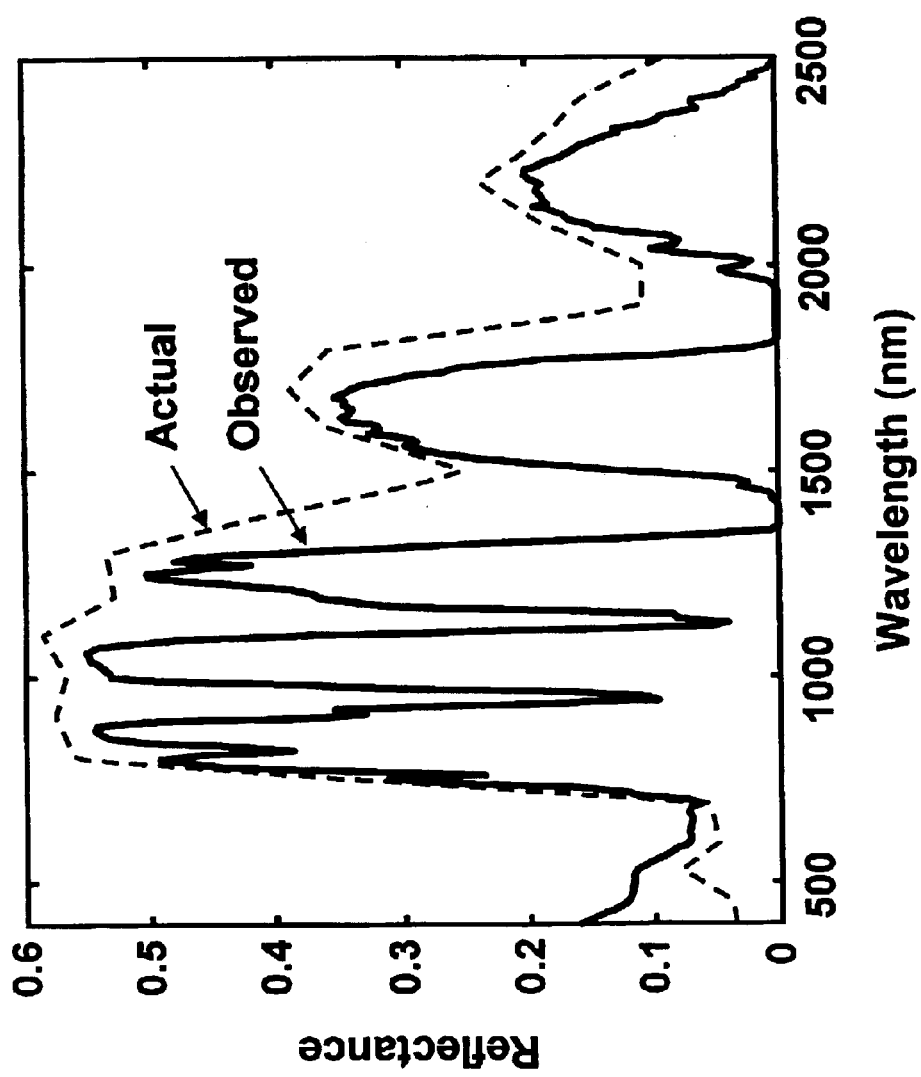
FIG. 1 is an example of observed and actual spectral reflectance curves of a vegetation-containing pixel for a nadir-viewing space-based sensor, useful in understanding the invention.
Figure 2:
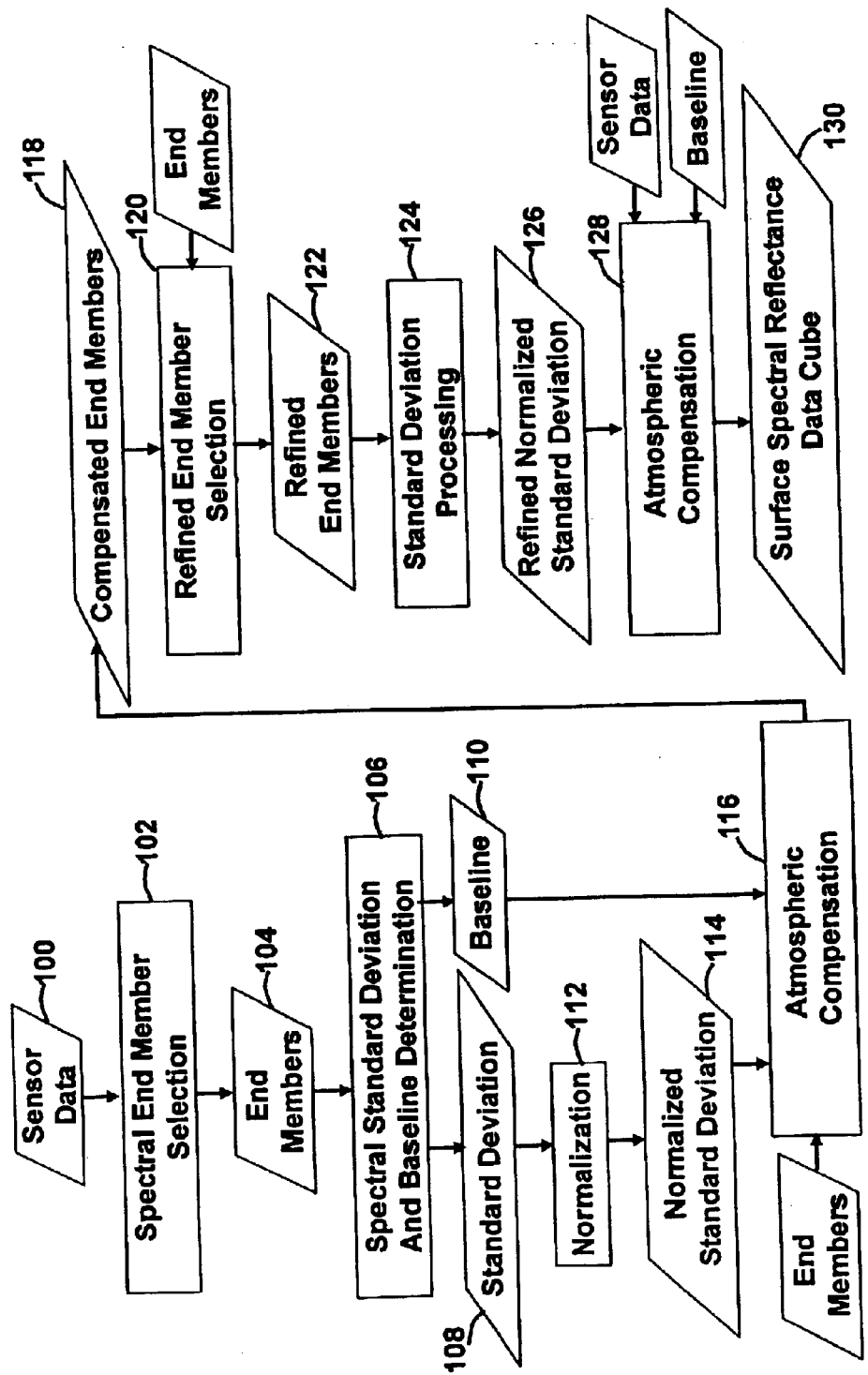
FIG. 2 is a data processing flow diagram for the preferred embodiment of the invention.

FIG. 2 depicts the data processing flow for the preferred embodiment. The sensor data 100 is comprised of multi- or hyperspectral imagery in which at least two spectral bands below 3000 nm are available. There is no upper limit to the number of spectral bands that can be handled. The input data can be in units of calibrated radiance or apparent spectral reflectance or even in uncalibrated raw counts. The choice of units only impacts the selection of normalization method 112.

A spectral end member selection algorithm 102 is used to select a plurality of spectrally-diverse pixels. While there are a number of suitable end member algorithms, the Spectral Sciences, Inc. SMACC (Sequential Maximum Angle Convex Cones) algorithm was utilized for its excellent computational efficiency. Other methods for selecting a diverse set of pixel spectra will be known to those skilled in the art, and may include clustering algorithms as well as end member algorithms; however, clustering algorithms are usually more computationally intensive. The precise number of end members used for the compensation is not critical. 10 to 20 end members is typically sufficient. An important aspect of SMACC is that it finds end members in order of decreasing spectral diversity. This can afford a significant computational efficiency, since the end member selection process can be terminated after the pre-selected number of end members is attained. For sensors containing more than ~10 spectral bands it is computationally efficient to limit the end member selection process to ~10 bands. Use of a subset of the total available number of bands does not impact the compensation quality as long as the selected subset spans the sensor spectral coverage.

Figure 3:
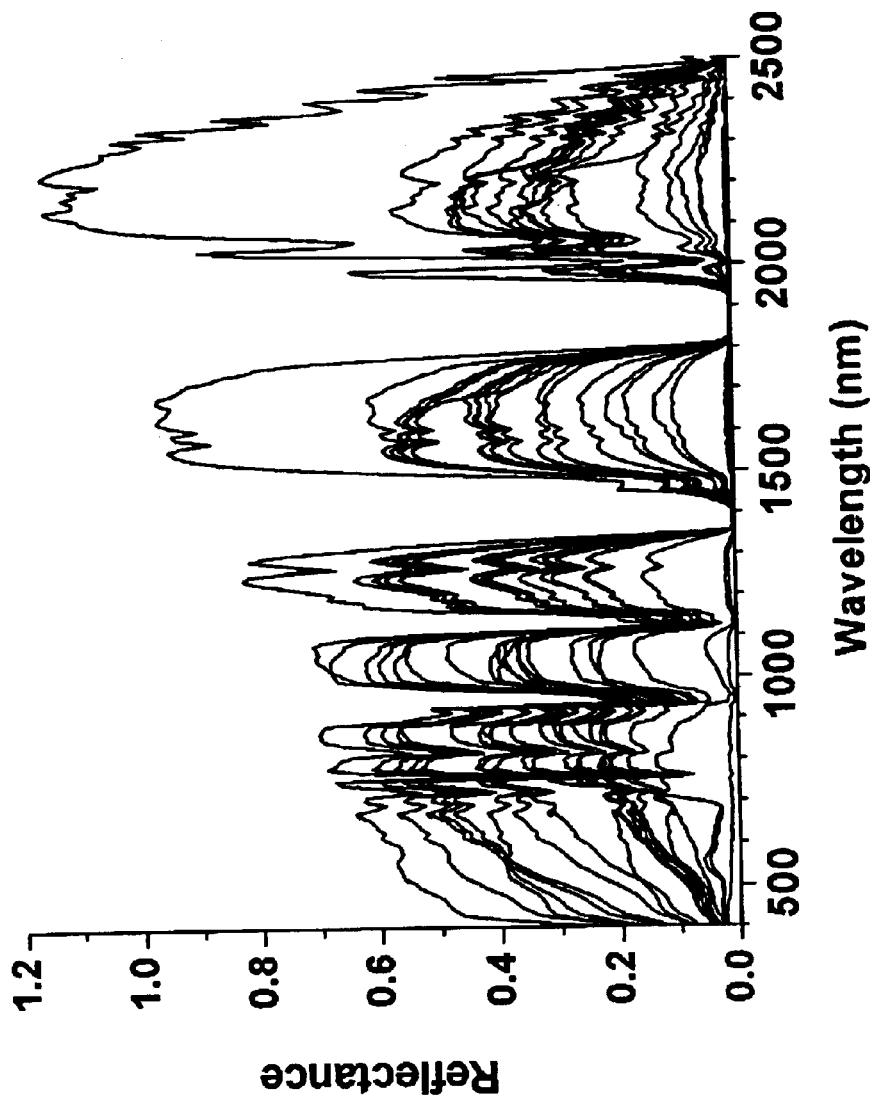
FIG. 3 shows selected spectral end members for a particular observation.

FIG. 3 displays end members selected from data taken by the airborne AVIRIS sensor (400–2500 nm, 224 bands, 512×512 scene pixels, 2 m GSD (Ground Sampling Distance)). Note the diversity of the selected spectra, a key aspect of this invention.

It is important to screen for and eliminate anomalous pixel spectra from the end member selection process. This includes pixels containing opaque clouds, thin cirrus clouds, and "bad" pixels containing sensor artifacts. Opaque clouds may be recognized using one of two methods, depending on the available sensor bands. If bands are available in either of the 940 nm or 1140 nm water vapor absorption bands, then opaque clouds can be recognized through anomalously small absorption depressions, as the clouds reside above most of the water vapor column. If the water bands are not available, then clouds can be recognized through a whiteness-brightness test; they are spectrally flat (white) and exhibit a high reflectance (bright). Thin cirrus is most easily flagged through an excess signal (cloud back scattering) in the very dark 1380 nm water absorption band. Cirrus clouds occur at much higher altitudes than other clouds, and thus are detectable even in very strongly absorbing water bands. Bad pixels are recognized through the presence of anomalously high (saturated) or low (negative) spectral channels. The screening thresholds for these types of anomalous pixels can be set conservatively. Since a reasonably large number of end members are selected, it does not matter if a few legitimate spectra are eliminated in the screening process.

Spectral standard deviation and baseline determination 106 are then performed on the selected end members. The methods for determining the baseline 110 and the conditions under which they are employed were described above. Similarly, for calibrated data, the methods for determining the normalization factor $g_o$ 112 were previously described. However, for uncalibrated data the normalization is determined and applied after the atmospheric compensation step 116. In this case, the brightest spectral channel from among all the compensated end members is scaled to unit reflectance; the required scaling factor is $g_o$.

Figure 4:
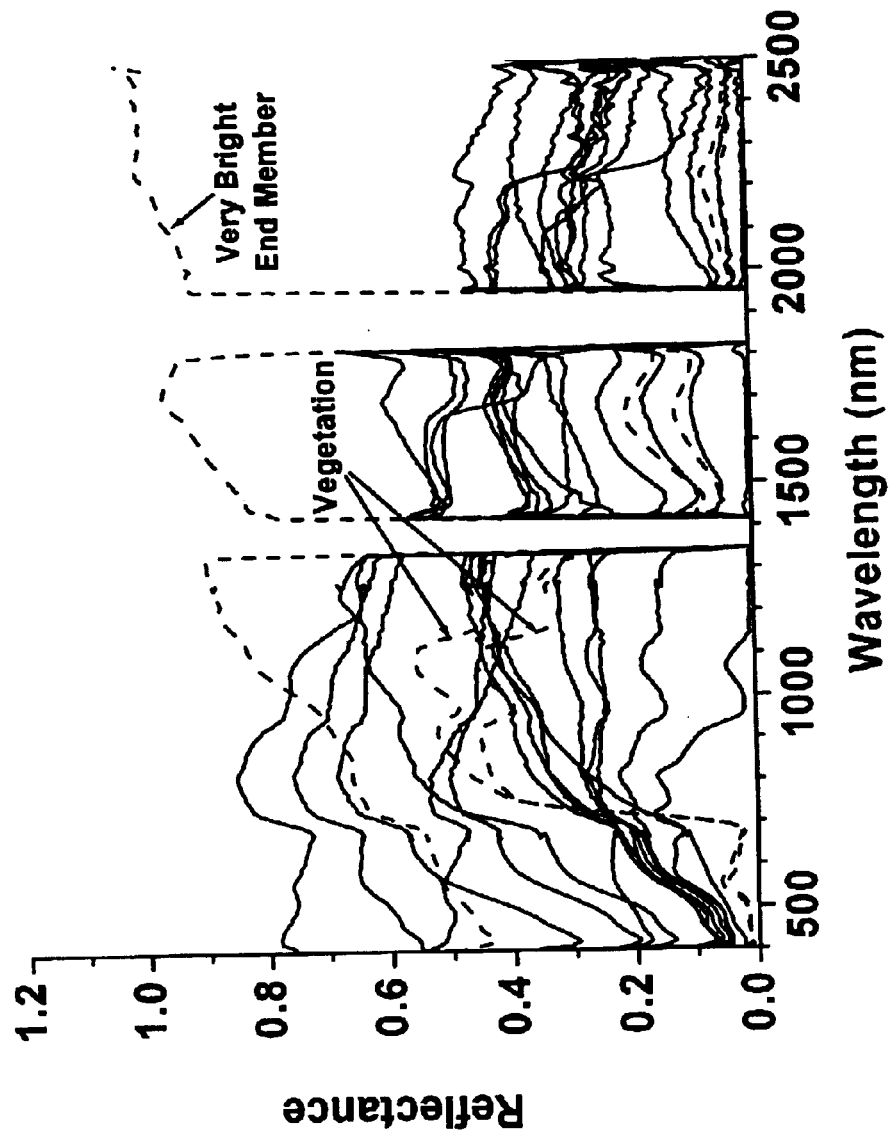
FIG. 4 shows normalized and atmospherically compensated end members of FIG. 3.
Figure 5:
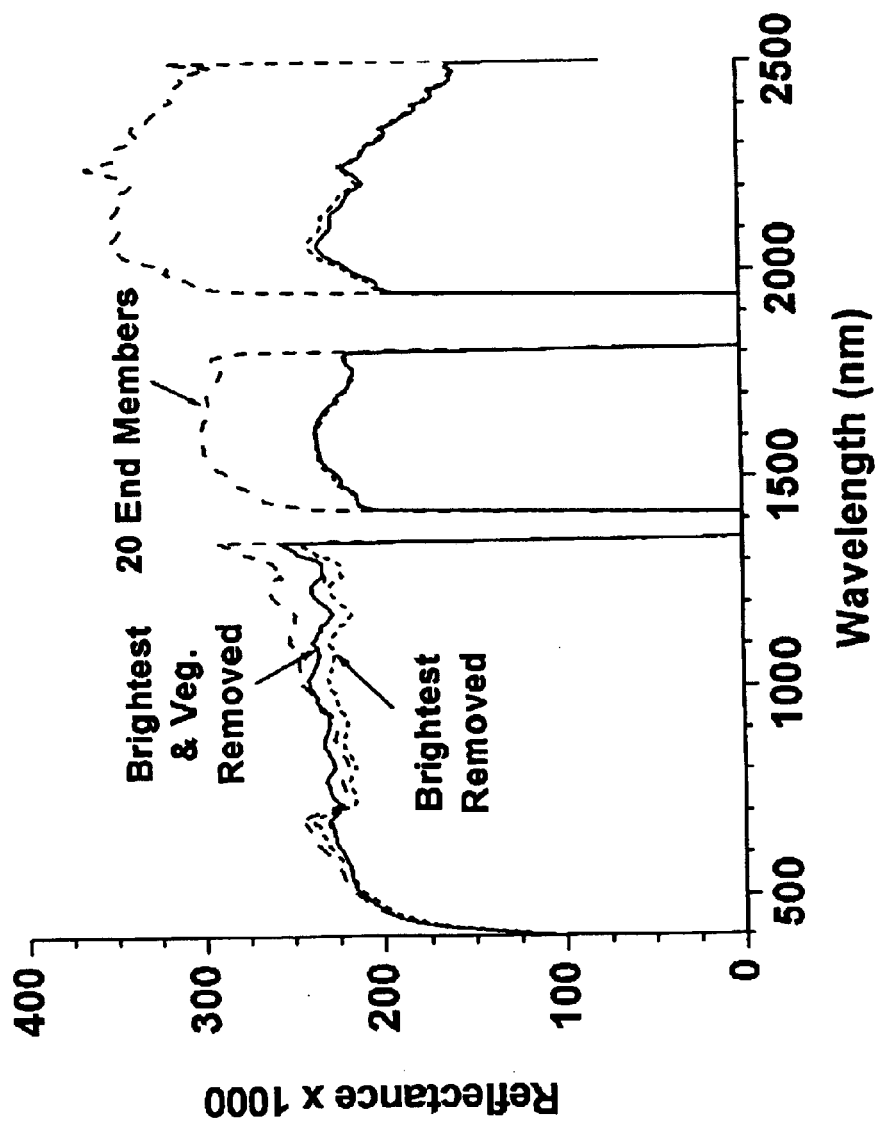
FIG. 5 shows the effect of the end member refinement process of the preferred embodiment.

Atmospheric compensation on the end members 116 is performed using Eq.(3). The resulting compensated end members 118 for the AVIRIS data are presented in FIG. 4. At this point, an improvement in the constancy of the standard deviation may be made by refining the end member selection 120 to remove end members that contain undesirable spectral features, generally characterized by an abrupt change in reflectance. This most often occurs for vegetation, which has a sharp red edge around 700 nm. As indicated in FIG. 4, there are vegetation end members for the AVIRIS data. It is straightforward to automatically identify and cull out vegetation spectra by searching for abrupt reflectance changes between bands on either side of the red edge. The improvement in the standard deviation due to removal of vegetation spectra is apparent in FIG. 5.

Further refinements of the end member selection may also be made by various methods. One method is to require that the end members be selected to agree with spectra contained in a library, or with linear combinations of such library spectra, to within a certain threshold. The library spectra may also be used to select or refine the value of the normalization factor $g_o$ to obtain the best fit between the normalized end members and the library spectra. In a generalization of the fitting step, a wavelength dependence may be introduced into the normalization factor $g_o$ such that the selected end members are made to agree with the corresponding library spectra as closely as possible. Another method for end member selection refinement is to require that the end members obey a requirement of spectral smoothness, such as by setting an upper limit on adjacent-channel differences; this represents a generalization of the vegetation exclusion method.

The refined end members undergo the same standard deviation processing 124 as comprised by steps 106, 108, and 112, resulting in the refined normalized standard deviation 126. Finally, atmospheric compensation 128 is performed on the entire sensor data set to yield the desired end product, the surface spectral reflectance data cube 130 (compensated spectra for all the pixels). This entails subtracting the baseline and dividing by the refined normalized standard deviation. The entire process flow is automated. Aside from the sensor data, the only externally required inputs are the solar elevation angle for each data set and specification of the available bands (band centers and widths) for the sensor.

Figure 6:
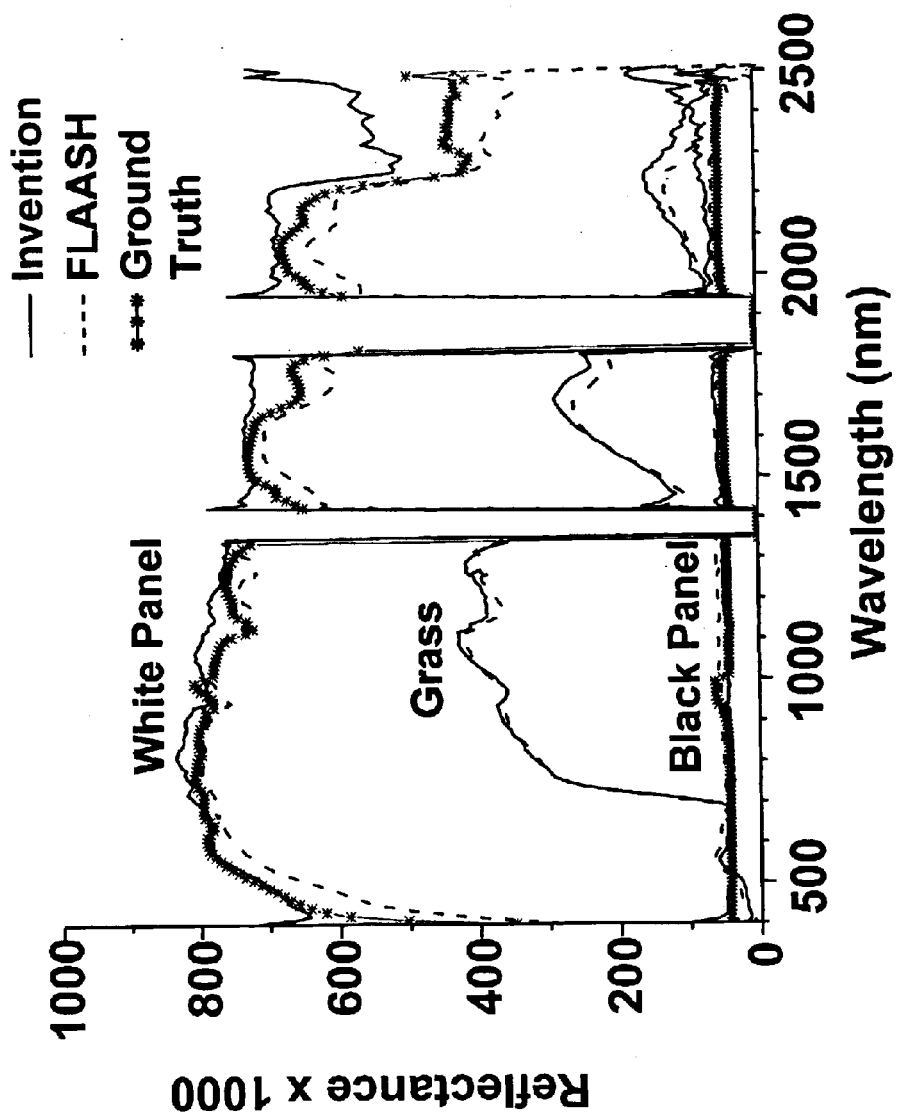
FIG. 6 is a comparison of atmospherically compensated hyper-spectral data of the invention to ground truth measurements and to compensated data based on the FLAASH code.
Figure 7:
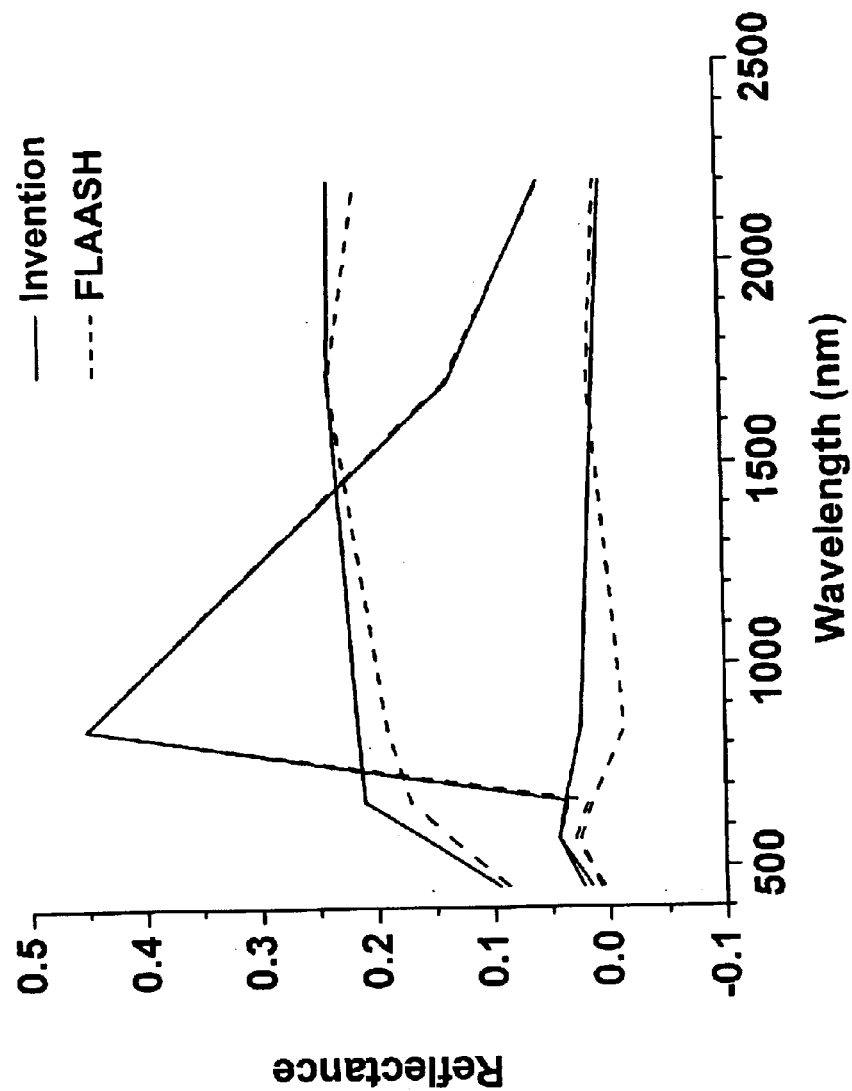
FIG. 7 is a comparison of atmospherically compensated multi-spectral data of the invention to compensated data based on the FLAASH code.

The quality of the atmospheric compensation for the presentation invention can be assessed by comparison to results from one of the state-of-the-art atmospheric compensation codes, FLAASH. This comparison is provided in FIG. 6. FLAASH required ~10 min of computational time to perform its analysis whereas the present invention required under 1 min on the same computer (1.8 GHz Pentium IV PC). This invention also works well for multi-spectral satellite data such as from the Landsat7 ETM+ sensor (6 bands in the 450–2500 nm region with a 30 m GSD), as shown in FIG. 7.

Figure 8:
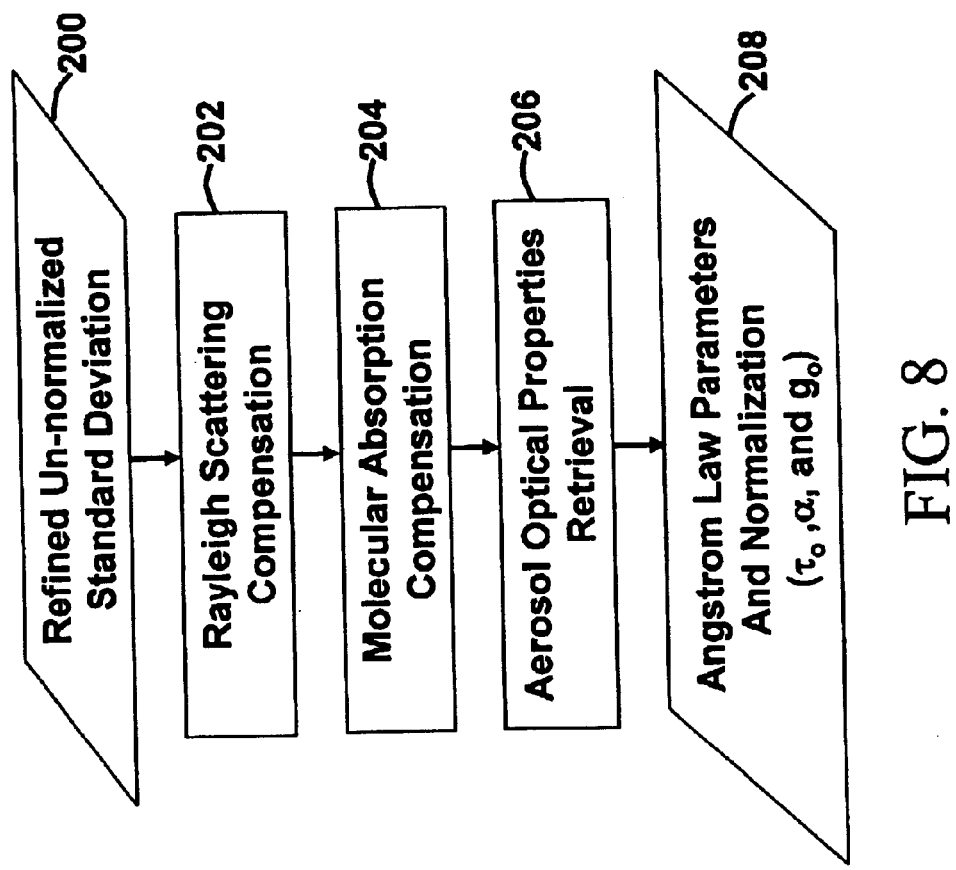
FIG. 8 is a data processing flow diagram for the preferred embodiment of the aerosol optical properties retrieval method of the invention.
Figure 9:
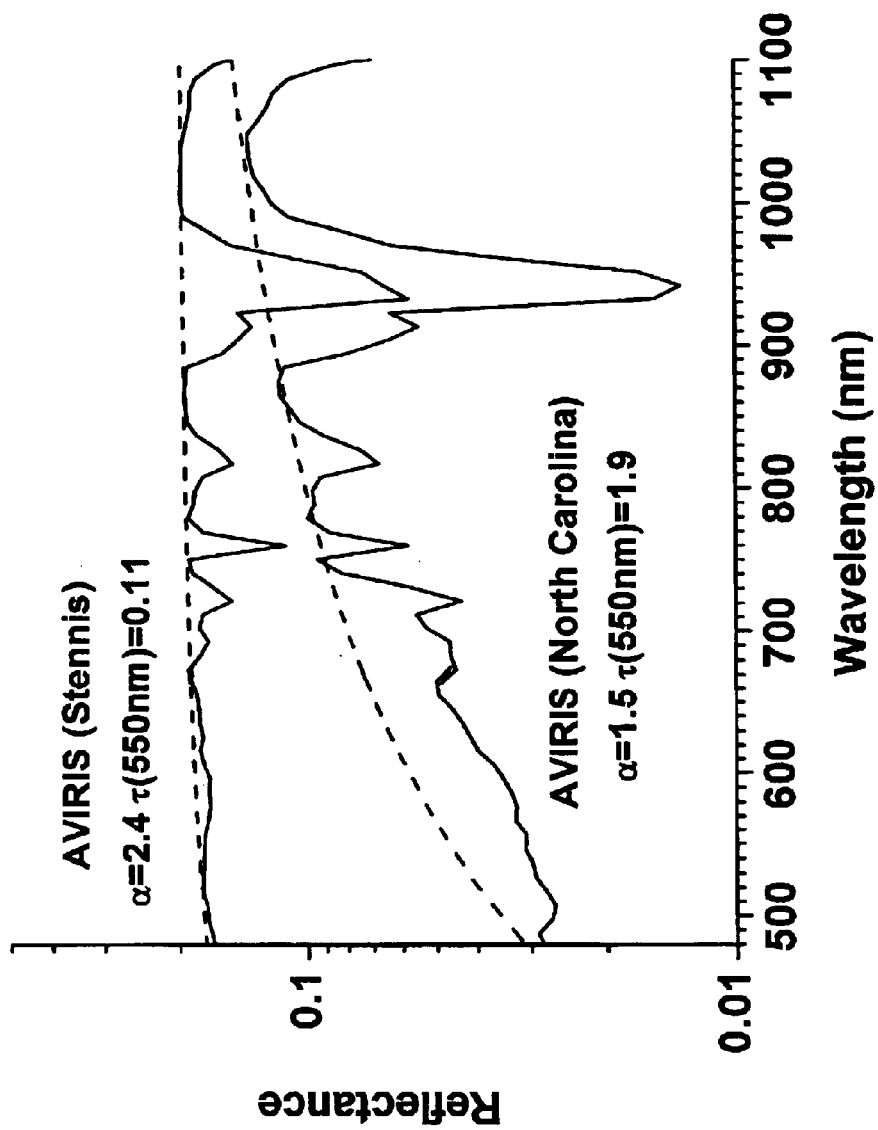
FIG. 9 depicts examples of aerosol optical properties retrieval of the invention for both clear and hazy data.

The preferred embodiment for the aerosol optical properties retrieval is presented in FIG. 8. The starting point for the aerosol properties retrieval is the refined un-normalized standard deviation 200 which derives from the standard deviation processing 124 (see FIG. 2) of the end members. The un-normalized standard deviation is first corrected for sun-surface-sensor transmittance losses due to Rayleigh scattering. This may be accomplished either through the use of an accurate radiative-transfer code (e.g., MODTRAN) or through well-established and accurate analytical approximations. While it is generally preferred to select bands outside of the molecular absorption bands, this is not also possible for some sensors. In these cases, the molecular absorption effects 204 can be corrected through the use of an accurate radiative-transfer code in concert with specification of the molecular absorber column amounts. The molecular column amounts may be obtained either by retrieval from the un-normalized spectral standard deviation 200 itself if suitable bands are available using an atmospheric compensation code such as FLAASH or by estimation based on a climatology data base or measured weather conditions. The aerosol optical properties retrieval 206 is performed on the Rayleigh scattering and molecular absorption compensated data. It proceeds in two steps. First, the bands selected for the aerosol retrieval are ratioed to a reference band and the resulting ratios are fit using the Angstrom formula in Eq.(6). This results in the reference optical depth $\tau_o$ and wavelength scaling exponent $\alpha$. Second, this also enables a more exact determination of the normalization constant using Eq.(8), which can be employed in the atmospheric compensation processing. The use of the aerosol retrieval algorithm is illustrated in FIG. 9 for examples of clear and hazy data obtained by the AVIRIS sensor.

The molecular optical properties for each molecular absorption feature can also be retrieved from the un-normalized spectral standard deviation 200. This requires at least three bands, a molecular absorption band and two nearby, preferably flanking, reference bands (no molecular absorption). By linear interpolation or extrapolation, the reference bands are used to estimate the zero-absorption signals for each absorption band. The ratio of the absorption band signals to their corresponding zero-absorption signals define the molecular transmittance function $T(\lambda)$. The molecular optical depths can be retrieved from $\tau(\lambda)=-\ln T(\lambda)$. If the spectral absorption coefficients $\alpha(\lambda)$ are known for the band, then the molecular column amount U can be retrieved from a single wavelength by $U=\tau(\lambda)/\alpha(\lambda)$.

Although specific features of the invention are shown in some drawings and not others, this is for convenience only as some feature may be combined with any or all of the other features in accordance with the invention.

Other embodiments will occur to those skilled in the art and are within the following claims:

What is claimed is:

1. A method of automatically compensating a multi- or hyper-spectral, multi-pixel image for atmospheric effects, comprising:

resolving a plurality of spectrally-diverse pixels from the image;

determining a spectral baseline from the spectrally-diverse pixels;

determining a statistical spectral deviation of the spectrally-diverse pixels;

normalizing the statistical spectral deviation by applying a scale factor; and compensating image pixels with both the spectral baseline and the normalized spectral deviation.

2. The image compensation method of claim 1 wherein the compensating step comprises subtracting the spectral baseline from the image pixels to accomplish partially-compensated pixels.

3. The image compensation method of claim 2 wherein the compensating step further comprises dividing the partially-compensated pixels by the normalized spectral deviation.

4. The image compensation method of claim 1 wherein the resolving step takes place with a spectral end member selection algorithm.

5. The image compensation method of claim 1 wherein the resolving step takes place with a clustering algorithm.

6. The image compensation method of claim 1 wherein the resolving step is accomplished manually.

7. The image compensation method of claim 1 wherein at least ten end members are resolved.

8. The image compensation method of claim 1 wherein the resolving step takes place using a subset of spectral bands that span the spectrum of the image.

9. The image compensation method of claim 1 further comprising screening anomalous pixels out of the image pixels before the resolving step.

10. The image compensation method of claim 9 wherein the screening step comprises removing pixels containing clouds.

11. The image compensation method of claim 1 wherein the spectral baseline determining step takes place using a linear regression method.

12. The image compensation method of claim 1 wherein the spectral baseline determining step comprises determining the excess reflectance at relatively short wavelengths relative to a flat spectral reflectance material.

13. The image compensation method of claim 1 wherein the spectral baseline determining step comprises determining the darkest signal from all of the image pixels for each spectral band.

14. The image compensation method of claim 1 wherein the spectral baseline determining step comprises determining the darkest signal in any spectral band from all of the spectrally-diverse pixels.

15. The image compensation method of claim 14 wherein the spectral baseline determining step comprises subtracting a constant reflectance contribution.

16. The image compensation method of claim 15 wherein the spectral baseline determining step further comprises setting the constant reflectance contribution to match the darkest signal at a reference wavelength.

17. The image compensation method of claim 1 wherein the spectral baseline determining step is based on using a radiative-transfer code to compute the baseline based on the determined aerosol and molecular optical properties.

18. The image compensation method of claim 1 wherein the statistical spectral deviation determining step comprises determining the standard deviation of the spectrally-diverse pixels.

19. The image compensation method of claim 1 wherein the normalizing step comprises normalizing in a spectral band in which the sun-surface-sensor path spectral transmittance factor is close to unity.

20. The image compensation method of claim 1 wherein the normalizing step comprises resolving at least two spectral window bands that do not have a significant contribution from water absorption, correcting for Rayleigh scattering, using the spectral deviations of these window bands to retrieve an aerosol optical depth, and using the optical depth to normalize.

21. The image compensation method of claim 1 wherein the normalizing step involves establishing the scale factor such that the maximum retrieved reflectance value for any wavelength and pixel of the spectrally-diverse pixels is unity.

22. The image compensation method of claim 1 wherein the normalizing step comprises comparing the spectrally-diverse pixels to a predetermined set of spectra of different, known materials.

23. The image compensation method of claim 1 further comprising refining the spectrally-diverse pixels to remove spectrally-diverse pixels that contain undesirable spectral features, the refining step taking place after the normalizing step and before the compensating step.

24. The image compensation method of claim 23 wherein the refining step comprises removing pixels with an abrupt reflectance change around about 700 nm.

25. The image compensation method of claim 23 wherein the refining step comprises removing pixels that have the greatest effect on the smoothness of the statistical spectral deviation.

26. The image compensation method of claim 23 wherein the refining step comprises introducing a wavelength dependence into a normalization factor such that selected spectrally-diverse pixels are made to agree with corresponding known library spectra as closely as possible.

* * * * *